United States Patent [19]

Yamanaka et al.

[11] Patent Number: 4,547,585
[45] Date of Patent: Oct. 15, 1985

[54] PROCESS FOR PREPARING TETRAKIS [3-(3,5-DIBUTYL-4-HYDROXYPHENYL)-PROPIONYLOXYMETHYL] METHANE

[75] Inventors: Toru Yamanaka, Otake; Tadatoshi Yoshimura, Iwakuni, both of Japan

[73] Assignee: Mitsui Petrochemical Industries, Ltd., Tokyo, Japan

[21] Appl. No.: 381,874

[22] Filed: May 25, 1982

[30] Foreign Application Priority Data

May 28, 1981 [JP] Japan ................................. 56-80123

[51] Int. Cl.[4] ............................................. C07C 69/76
[52] U.S. Cl. ...................................... 560/075; 562/478
[58] Field of Search ........................................... 560/75

[56] References Cited

U.S. PATENT DOCUMENTS 4,085,132  4/1978  Park et al. ............................ 560/075

FOREIGN PATENT DOCUMENTS 288839  4/1967  Australia ............................... 560/075
56-12341 2/1981  Japan ..................................... 560/075

Primary Examiner—Paul J. Killos
Attorney, Agent, or Firm—Cushman, Darby & Cushman

[57] ABSTRACT

Tetrakis [3-(3,5-dibutyl-4-hydroxyphenyl)propionyloxymethyl] methane having a high purity and excellent whiteness is prepared. In this process, an ester exchange reaction between a propionic acid ester having the general formula:

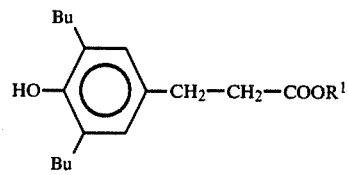

wherein Bu is an n-, sec-, iso-, or tert-butyl group and $R^1$ is an alkyl group having 1 to 4 carbon atoms, and pentaerythritol in the presence of an alkaline catalyst is effected by adding 0.2 through 1.8 mol of water based on 1 mol of the alkaline catalyst by the substantial completion of the ester exchange reaction.

9 Claims, No Drawings

PROCESS FOR PREPARING TETRAKIS [3-(3,5-DIBUTYL-4-HYDROXYPHENYL)PROPIONYLOXYMETHYL] METHANE

The present invention relates to a process for preparing tetrakis [3-(3,5-dibutyl-4-hydroxyphenyl)propionyloxymethyl]methane.

Tetrakis [3-(3,5-dibutyl-4-hydroxyphenyl)propionyloxymethyl]methanes having the general formula:

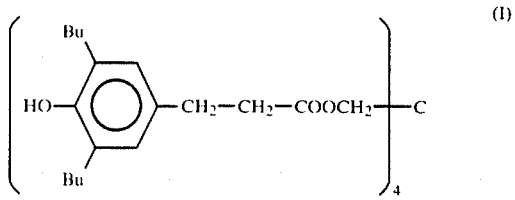

wherein Bu is an n-, sec-, iso-, or tert-butyl group, are preferably used as stabilizers for rubbers, plastics, and other various polymers.

It is known that compounds having general formula (I) are prepared by the steps of:

(A) reacting an alkyl acrylate having the general formula:

$$CH_2=CH-COOR^1 \quad (II)$$

wherein $R^1$ is an alkyl group having 1 to 4 carbon atoms, with 2.6-dibutylphenol, thereby forming a propionic acid ester having the general formula:

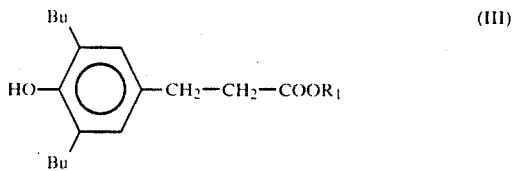

wherein Bu and $R^1$ are the same as defined above; and (B) effecting an ester exchange reaction between the propionic acid ester having the general formula (III) and pentaerythritol without isolating said propionic acid ester (see U.S. Pat. No. 4,085,132).

This process is practically advantageous in that the isolation and purification operations of the intermediate product (III) from the reaction product at step (A) can be omitted and the catalyst used at the step (A) can be reused at the subsequent step (B) as is, since isolation of the ester (III) is not necessary. However, this process is disadvantageous in that by-products formed together with the desired intermediate product (III) at step (A) are also subjected to the ester exchange reaction with pentaerythritol at step (B) and these by-products and the ester exchange reaction products thereof are included in the desired final product (I) as impurities, these being difficult to separate from the desired final product (I).

In order to solve these disadvantages, it has been proposed in Japanese Patent Application Laid-Open (Kokai) No. 56-12341 that the reaction temperature and the mol ratio of the alkyl acrylate (II) to the 2.6-dibutylphenol at step (A) be limited to specific ranges, thereby decreasing the production amounts of the undesired by-products at step (A) and improving the purity of the desired final product (I).

The object of the present invention is to provide a process for preparing tetrakis [3-(3,5-dibutyl-4-hydroxyphenyl) propionyloxymethyl] methane in which the amount of the undesired by-products or impurities is remarkably decreased.

Another object of the present invention is to provide a process for preparing tetrakis [3-(3,5-dibutyl-4-hydroxyphenyl) propionyloxymethyl] methane at an improved yield, purity, and whiteness without having to isolate the intermediate ester (III), as compared with the process disclosed in Japanese Patent Application Laid-Open No. 56-12341.

Other objects and advantages of the present invention will be apparent from the following description.

In accordance with the first embodiment of the present invention, there is provided a process for preparing tetrakis [3-(3,5-dibutyl-4-hydroxyphenyl)propionyloxymethyl] methane, wherein an ester exchange reaction between a propionic acid ester having the general formula:

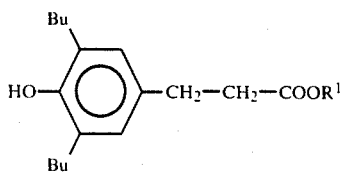

wherein Bu is an n-, sec-, iso-, or tert-butyl group and $R^1$ is an alkyl group having 1 to 4 carbon atoms, and pentaerythritol in the presence of an alkaline catalyst is effected by adding 0.2 through 1.8 mol of water based on 1 mol of the alkaline catalyst by the substantial completion of the ester exchange reaction. This ester exchange reaction is referred to as "the reaction of step (B)" or "step (B)" herein.

In accordance with the second embodiment of the present invention, there is also provided a process for preparing tetrakis [3-(3,5-dibutyl-4-hydroxyphenyl)propionyloxymethyl] methane comprising the steps of:

(A) reacting an alkyl acrylate having the general formula:

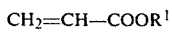

$$CH_2=CH-COOR^1$$

wherein $R^1$ is an alkyl group having 1 to 4 carbon atoms, with 2.6-dibutylphenol in the presence of an alkaline catalyst, thereby forming a reaction product containing a propionic acid ester having the general formula:

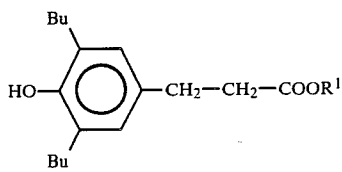

wherein Bu is an n-, sec-, iso-, or tert-butyl group, and $R^1$ is the same as defined above, and distilling off the unreacted starting materials from the reaction product; and (B) effecting an ester exchange reaction of the resultant reaction product and pentaerythritol by adding 0.2 through 1.8 mol of water based on 1 mol of the alkaline catalyst between the completion of the addition reaction of step (A) and the substantial completion of the ester exchange reaction.

According to the present invention, the addition of the specified amount of water at step (B) remarkably decreases the amount of undesired impurities produced, these impurities believed to be the addition products of the intermediate ester (III) to the desired product (I). Thus, the purity of the desired product is remarkably increased. Furthermore, the addition of the specified amount of water at step (B) increases the reaction yield and the whiteness of the desired product, especially the transmittance at a wavelength of 425 nm.

The alkyl acrylate (II) is first reacted with 2,6-dibutylphenol, in the presence of the alkaline catalyst in a solvent at step (A) of the present invention, thereby forming the propionic acid ester having the above-mentioned general formula (III).

Examples of the alkyl acrylates (II) usable in the present invention are methyl acrylate, ethyl acrylate, propyl acrylate, and butyl acrylate. Methyl acrylate is most desirably used in the present invention.

Examples of the 2,6-dibutylphenols usable in the present invention are 2,6-di-tert-butylphenol, 2,6-di-sec-butylphenol, and 2,6-di-isobutylphenol. Of these 2,6-dibutylphenols, 2,6-di-tert-butylphenol is most desirably used in the present invention.

The mol ratio of the alkyl acrylate to the 2,6-dibutylphenol at step (A) can be varied within a wide range without affecting the desired advantages of the present invention. The recommendable mol ratio of the alkyl acrylate to the 2,6-dibutylphenol is within the range of from about 0.80 to about 1.07.

The alkaline catalysts usable in the present invention include, for example, sodium hydroxide, potassium hydroxide, lithium hydroxide, lithium aluminum hydride, sodium boron hydride, lithium hydride, sodium t-butoxide, potassium t-butoxide, sodium methoxide, potassium methoxide, sodium metal, and lithium metal. Especially desirable alkaline catalysts are the alcoxides of alkali metals such as sodium t-butoxide, potassium t-butoxide, sodium methoxide, and potassium methoxide. These alkaline catalysts are generally used in an amount of 0.5% through 8.0% by weight, desirably 1.0% through 5.0% by weight, based on the weight of the starting 2,6-dibutylphenol.

The addition reaction of step (A) of the present process can be carried out either in the presence of or in the absence of a solvent, although the use of a solvent is desirable. Examples of the solvents usable at step (A) of the present invention are dimethylformamide, dimethylacetamide, dimethylsulfoxide, hexamethylphosphoamide, acetonitrile, propionitrile, sulfonitrile, sulfolane, diglyme, tetrahydrofuran, and t-butyl alcohol. Especially, t-butyl alcohol is desirably used in the present invention. These solvents can be used in an amount of 5 parts by weight or less, desirably about 0.1 through about 1 part by weight, based on 1 part by weight of the starting 2,6-dibutylphenol.

The reaction conditions of the addition reaction of step (A) of the present invention can be varied within wide ranges. For instance, the reaction temperature is generally about 70° C. through about 100° C., desirably about 80° C. through about 95° C. The reaction pressure can be either normal atmospheric pressure or an elevated pressure, desirably atmospheric pressure through 5 kg/cm$^2$G. The reaction time can be generally 2 through 10 hours, desirably 6 through 8 hours. The reaction is desirably carried out under stirring in any type of conventional reaction vessel provided with a stirrer.

After the addition reaction of step (A) is completed, the unreacted alkyl acrylate (II) is distilled off from the reaction product. Any conventional distillation method can be used. The resultant reaction product is directly used as the starting material at the subsequent step (B) of the second embodiment of the present invention. It should be, however, noted that the propionic acid ester having the general formula (III) produced by any methods can be used as a starting material in the ester exchange reaction of the first embodiment of the present invention.

The resultant reaction product including the desired propionic acid ester (III) is reacted with pentaerythritol at step (B) of the present invention in the conventional manner. Thus, the desired tetrakis [3-(3,5-dibutyl-4-hydroxyphenyl)propionyloxymethyl] methane includes tetrakis [3-(3,5-di-tert-butyl-4-hydroxyphenyl)propionyloxymethyl] methane, tetrakis [3-(3,5-di-sec-butyl-4-hydroxyphenyl) propionyloxymethyl] methane, and tetrakis [3-(3,5-diisobutyl-4-hydroxyphenyl)propionyloxymethyl] methane. Tetrakis [3-(3,5-di-tert-butyl-4-hydroxyphenyl)propionyloxymethyl] methane is especially desirably prepared by the present invention.

The mol ratio of the pentaerythritol to the intermediate propionic acid ester (III) is generally 1/4 through 1/5, desirably 1/4.2 through 1/4.6, although the ester exchange reaction of the present invention is not limited to these ranges.

The ester exchange reaction of step (B) of the present invention proceeds in such a manner that the ester group of the intermediate propionic acid ester (III) is reacted with the hydroxide groups of the pentaerythritol to form an alcohol such as methanol. This ester exchange reaction can be catalyzed by any catalyst conventionally used in the ordinary ester exchange reaction. Such catalysts are those usable at step (A) of the second embodiment of the present invention mentioned hereinabove. These alkaline catalysts are generally used in an amount of 0.4% through 8.0% by weight, desirably 0.8% through 5.0% by weight, based on the weight of the propionic acid ester (III). However, in the second embodiment of the present invention, the alkaline catalysts used in the previous step (A) of the present invention and still contained in the resultant product of step (A) can be desirably used at step (B) of the present invention. Furthermore, the amount of the catalyst remaining in the resultant reaction product of step (A) of the present invention is sufficient to catalyze the ester exchange reaction of step (B) of the present invention and, therefore, no further addition of the catalyst at step (B) is required.

The ester exchange reaction of step (B) is desirably carried out in a solvent. The solvents used at step (A) of the present invention can also be used in the reaction of step (B). Of course the solvent or another solvent be optionally added to the reaction mixture at step (B) in cases that the solvent is removed together with the unreacted alkyl acrylate at the distillation step.

The term "the substantial completion of the ester exchange reaction" used herein means such a condition that no substantial change, within analytical error, is observed in the yield of the desired product (I) when the ester exchange reaction is continued for a further 2 hours. The ester exchange reaction is generally carried out at a temperature of about 80° C. through about 140° C. under reduced pressure for about 5 through 10 hours, although the present invention is not limited to these conditions.

According to the present invention, about 0.2 through 1.8 mol, desirably about 0.5 through 1.5 mol, of water based on 1 mol of the alkaline catalyst should be added at step (B) of the present invention. The water can be added to the reaction mixture at any time by the substantial completion of the ester exchange reaction in the first embodiment of the present invention or between the completion of the addition reaction of step (A) and the substantial completion of the ester exchange reaction of step (B) in the second embodiment of the present invention. The water is desirably added at the time just before the addition of the pentaerythritol, at the same time as the addition of the pentaerythritol, or after the initiation of the ester exchange reaction by the addition of the pentaerythritol. It is especially recommended that the addition of water be started at the stage when the yield of the desired product (I) becomes approximately 70% or more, especially approximately 80% through 90%. Thus, the yield, purity, and whiteness of the desired product are remarkably improved. The water may be added all at once, continuously, or intermittently. Less than 0.2 mol of the water based on 1 mol of the alkaline catalyst does not result in the desired improvements in the purity and whiteness of the desired product (I). Contrary to this, more than 1.8 mol of the water based on 1 mol of the alkaline catalyst decreases the yield of the desired product (I), although the purity and whiteness are improved.

The alcohol such as methanol formed in the ester exchange reaction of step (B) is removed at any time during the reaction from the reaction mixture. The removal of the alcohol can be effected by any known manner, for example, by distilling off under a reduced pressure of about 5 through 50 mmHg.

The ester exchange reaction of step (B) can be carried out in any conventional reaction vessel. Especially, according to the present invention, the reaction vessel used at step (A) is directly used in the subsequent step (B) without withdrawing the reaction product of step (A). The reaction vessels are desirably provided with, for example, stirring unit, a heating apparatus, an addition device and a distillation apparatus.

The desired reaction product (I) is isolated from the reaction mixture and purified. The isolation and purification is desirably carried out by means of a recrystallization method. Examples of the solvents usable in the recrystallization are hexane, cyclohexane, heptane, ethanol, isopropanol, n-propanol, isobutanol, sec-butanol, and n-butanol. Especially, it is desirable that medium alcohols such as isopropanol, n-propanol, isobutanol, sec-butanol or n-butanol are used as a solvent for recrystallization and the desired product (I) is crystallized as an adduct of these alcohols.

According to the isolation and purification operation by means of the recrystallization method, the desired product (I) contained in the reaction product of step (B) is advantageously recovered at a high yield and at a high purity.

As mentioned hereinabove, according to the present invention, the desired tetrakis [3-(3,5-dibutyl-4-hydroxyphenyl) propionyloxyphenyl] methane having an improved purity and whiteness is prepared at an improved yield, without isolating the intermediate product (III) from the reaction product of the step (A), by the addition of the specified catalytic amount of water during the ester exchange reaction of step (B). Accordingly, the tetrakis [3-(3,5-dibutyl-4-hydroxyphenyl) propionyloxyphenyl] methane thus obtained is suitable for use as stabilizers for rubbers and plastics especially due to the improvement in the whiteness thereof.

The present invention now will be further illustrated by, but is by no means limited to, the following Examples.

EXAMPLE 1

Twenty six milliliters of tert-butanol, 1.42 g of potassium tert-butoxide, 93.25 g of 2,6-di-tert-butyl-phenol (a), and 39.69 g of methyl acrylate (b) (i.e., the mol ratio of the compounds (b)/(a)=1.02) were added, under a nitrogen atmosphere, to a 500 ml 4-necked flask provided with a stirrer, a reflux condenser, a thermometer, and a nitrogen feed pipe and were allowed to react at a temperature of 87° C. for 8 hours with stirring. The flask was reduced under a pressure of 30 mmHg, whereby the unreacted methyl acrylate was distilled off. Thereafter, the pressure was raised to atmospheric pressure by feeding nitrogen to the flask.

As a result of a gas chromatograph analysis of the reaction product obtained in the above-mentioned step (A), it was observed that the desired intermediate product, 3-(3,5-di-tert-butyl-4-hydroxyphenyl) methylpropionate was obtained at a yield of 96.5% based on the starting 2,6-di-tert-butylphenol.

Thereafter, 13.37 g of pentaerythritol (corresponding to 1/4.4 mol of the 2,6-di-tert-butylphenol), 50 g of dimethylformamide, and 0.22 g of water were added to the reaction mixture obtained above. The mixture was first stirred at a temperature of 87° C. for 10 minutes and, then, allowed to react at a temperature of 90° C. under a pressure of 30 mmHg for 1 hour, while the formed methanol was distilled off. Then, the reaction mixture was allowed to stand at a temperature of 100 through 140° C. under a pressure of 20 mmHg for 6 hours, whereby the dimethylformamide was distilled off and the ester exchange reaction was completed.

Thereafter, nitrogen was introduced to the flask to return the pressure to atmospheric pressure and the reaction mixture was neutralized with glacial acetic acid. As a result of a gas chromatograph analysis of the reaction product obtained at step (B), it was observed that the desired final product was obtained at a yield of 92.1% based on the pentaerythritol.

The resultant sticky solid was recrystallized from 90% isopropanol to crystallize the desired product as an addition product. The crystallized product was dried. Thus, 103.6 g of the white crystal having a purity of 98.3% and containing 0.32% by weight of an addition product of the intermediate ester (III) to the desired product (I) (i.e., by-product), which was determined at a UV radiation of 254 nm by means of a high velocity liquid chromatography utilizing a Zorbax Sil ® (available from Shimadzu Corporation) column, was obtained.

Thirty grams of the crystal obtained above was dissolved in 100 ml of toluene. The transmittance of this solution at a wavelength of 425 nm was 96.1%.

EXAMPLES 2 AND 3 AND COMPARATIVE EXAMPLES 1 AND 2

Example 1 was repeated except that the addition amount of the water at step (B) was changed as shown in Table 1 below.

The results are shown in Table 1.

TABLE 1

| No. | Water/ Alkaline Cat. (mol ratio) | Yield (%) | Purity (%) | Transmittance (%) | Content of by-product* (%) |
|---|---|---|---|---|---|
| Example 1 | 1.0 | 92.1 | 98.3 | 96.1 | 0.32 |
| Example 2 | 0.5 | 93.3 | 97.5 | 94.1 | 0.45 |
| Example 3 | 1.5 | 91.3 | 98.2 | 95.5 | 0.25 |
| Comparative Example 1 | 0 | 91.1 | 97.0 | 92.4 | 1.92 |
| Comparative Example 2 | 2.0 | 78.3 | 97.5 | 96.6 | 0.10 |

*which is seemed to be the addition product of the intermediate product (III) to the desired final product (I).

As is clear from the results shown in Table 1, the products obtained in Examples 1 to 3 according to the present invention have an improved purity and excellent whiteness as compared with that obtained in Comparative Example 1 in which no water was added. Furthermore, the yield of the desired product was low in Comparative Example 2 in which an excess amount of water was used.

Examples 4 and 5

Example 1 was repeated except that the mol ratio of the methyl acrylate to the 2,6-di-tert-butylphenol at step (A) was changed to 0.90 and 0.96.

The results are shown in Table 2 below.

EXAMPLES 6 and 7

Example 5 was repeated except that the addition time of the water during step (B) was changed as shown in Table 3 below. The addition of the water was carried out all at once.

The results are shown in Table 3.

TABLE 2

| Example No. | Acrylate/Dibutylphenol (mol ratio) | Water/Catalyst (mol ratio) | Yield (%) | Purity (%) | Transmittance (%) | Content of by-product (%) |
|---|---|---|---|---|---|---|
| 4 | 0.9 | 1.0 | 93.0 | 99.1 | 95.0 | 0.28 |
| 5 | 0.96 | 1.0 | 93.5 | 98.5 | 94.4 | 0.19 |
| 1 | 1.02 | 1.0 | 92.1 | 98.3 | 96.1 | 0.32 |

TABLE 3

| Example No. | Water addition time*1 (hr) | Yield (%) | Purity (%) | Transmittance (%) | Content of by-product (%) |
|---|---|---|---|---|---|
| 5 | 0*2 | 93.5 | 98.5 | 94.4 | 0.19 |
| 6 | 5*3 | 93.1 | 98.6 | 94.4 | 0.17 |
| 7 | 6.5*4 | 93.6 | 99.1 | 96.6 | 0.23 |

*1Time from the addition of the pentaerythritol
*2Simultaneously with the addition of the pentaerythritol
*3The desired product was formed at a yield of approximately 50-60%.
*4The desired product was formed at a yield of approximately 80-90%.

We claim:

1. A process for preparing tetrakis [3-(3,5-dibutyl--4-hydroxyphenyl)propionyloxymethyl] methane, wherein an ester exchange reaction between a propionic acid ester having the general formula:

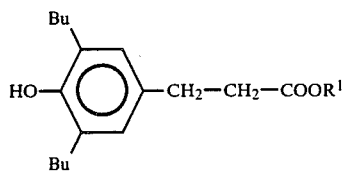

wherein Bu is an n-, sec-, iso-, or tert-butyl group and $R^1$ is an alkyl group having 1 to 4 carbon atoms, and pentaerythritol in the presence of an alkaline catalyst is effected by adding 0.2 through 1.8 mol of water based on 1 mol of the alkaline catalyst by the substantial completion of the ester exchange reaction.

2. A process as claimed in claim 1 wherein the reaction temperature is 80° C. through 140° C.

3. A process as claimed in claim 1 wherein the mol ratio of the pentaerythritol to the propionic acid ester is ¼ through 1/5.

4. A process for preparing tetrakis [3-(3,5-dibutyl-4-hydroxyphenyl)propionyloxymethyl] methane, comprising the steps of:

(A) reacting an alkyl acrylate having the general formula:

$$CH_2=CH-COOR^1$$

wherein $R^1$ is an alkyl group having 1 to 4 carbon atoms, with 2,6-dibutylphenol in the presence of an alkaline catalyst, thereby forming a reaction product containing a propionic acid ester having the general formula:

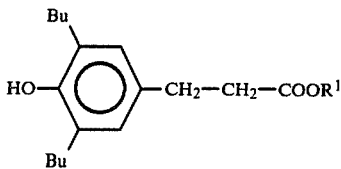

wherein Bu is an n-, sec-, iso-, or tert-butyl group and $R^1$ is the same as defined above, and distilling off the unreacted starting materials from the reaction product; and (B) effecting an ester exchange reaction between the resultant reaction product and pentaerythritol by adding 0.2 through 1.8 mol of water based on 1 mol of the alkaline catalyst between the completion of the addition reaction of step (A) and the substantial completion of the ester exchange reaction.

5. A process as claimed in claim 4 wherein the amount of the catalyst is 0.5% through 8.0% by weight based on 2,6-dibutylphenol.

6. A process as claimed in claim 4 wherein the reaction temperature of step (A) is 70° C through 100° C.

7. A process as claimed in claim 4 wherein the reaction temperature of step (B) is 80° C. through 140° C.

8. A process as claimed in claim 4 wherein the mol ratio of the alkyl acrylate to the 2,6-dibutylphenol is 0.80 through 1.07.

9. A process as claimed in claim 4 wherein the mol ratio of the pentaerythritol to the propionic acid ester is ¼ through 1/5.

* * * * *